(12) United States Patent
Nerot et al.

(10) Patent No.: US 11,229,522 B2
(45) Date of Patent: *Jan. 25, 2022

(54) MODULAR HUMERAL PROSTHESIS FOR AN INVERTED SHOULDER PROSTHESIS

(71) Applicants: DePuy Synthes Products, Inc., Raynham, MA (US); DEPUY IRELAND UNLIMITED COMPANY

(72) Inventors: Cecile Nerot, Reims (FR); Didier Capon, Sautron (FR); Ludwig Seebauer, Forstinning (DE); Anders Ekelund, Bromma (SE); Lieven De Wilde, Ghent (BE); Michael Wirth, San Antonio, TX (US); David Collins, Little Rock, AR (US); Laurent Lafosse, Annecy le Vieux (FR); Didier Poncet, Bron (FR)

(73) Assignees: DePuy Synthes Products, Inc.; DePuy Ireland Unlimited Company

( * ) Notice: Subject to any disclaimer, the term of this patent is extended or adjusted under 35 U.S.C. 154(b) by 0 days.

This patent is subject to a terminal disclaimer.

(21) Appl. No.: 15/455,422

(22) Filed: Mar. 10, 2017

(65) Prior Publication Data

US 2017/0181860 A1 Jun. 29, 2017

Related U.S. Application Data

(63) Continuation of application No. 11/577,966, filed as application No. PCT/FR2005/002663 on Oct. 25, 2005, now Pat. No. 9,622,869.

(30) Foreign Application Priority Data

Oct. 25, 2004 (FR) ........................ 0411366

(51) Int. Cl.
*A61F 2/40* (2006.01)
*A61F 2/30* (2006.01)

(52) U.S. Cl.
CPC ........ *A61F 2/4014* (2013.01); *A61F 2/30767* (2013.01); *A61F 2/4059* (2013.01);
(Continued)

(58) Field of Classification Search
CPC ............ A61F 2/4014; A61F 2002/4011; A61F 2002/4022; A61F 2002/4044; A61F 2002/407; A61F 2002/4074
See application file for complete search history.

(56) References Cited

U.S. PATENT DOCUMENTS

| 5,314,479 A | 5/1994 | Rockwood, Jr. |
| 5,358,526 A | 10/1994 | Tornier |

(Continued)

FOREIGN PATENT DOCUMENTS

| DE | 19841612 A1 | 3/2000 |
| EP | 0339530 A2 | 11/1989 |

(Continued)

OTHER PUBLICATIONS

Translation of EP0339530A2 retrieved from Espacenet on May 21, 2018.*

(Continued)

*Primary Examiner* — Megan Y Wolf

(57) ABSTRACT

The invention relates to a modular humeral prosthesis for an inverse shoulder prosthesis, comprising an anatomical shaft (1) and a separable epiphyseal head (2) which may be angularly orientated by rotation about the longitudinal axis (XX) of the anatomical shaft. The anatomical shaft and the epiphyseal head comprise complementary angular indexing means (11, 28) for relative rotational fixation.

5 Claims, 4 Drawing Sheets

Figure 1:
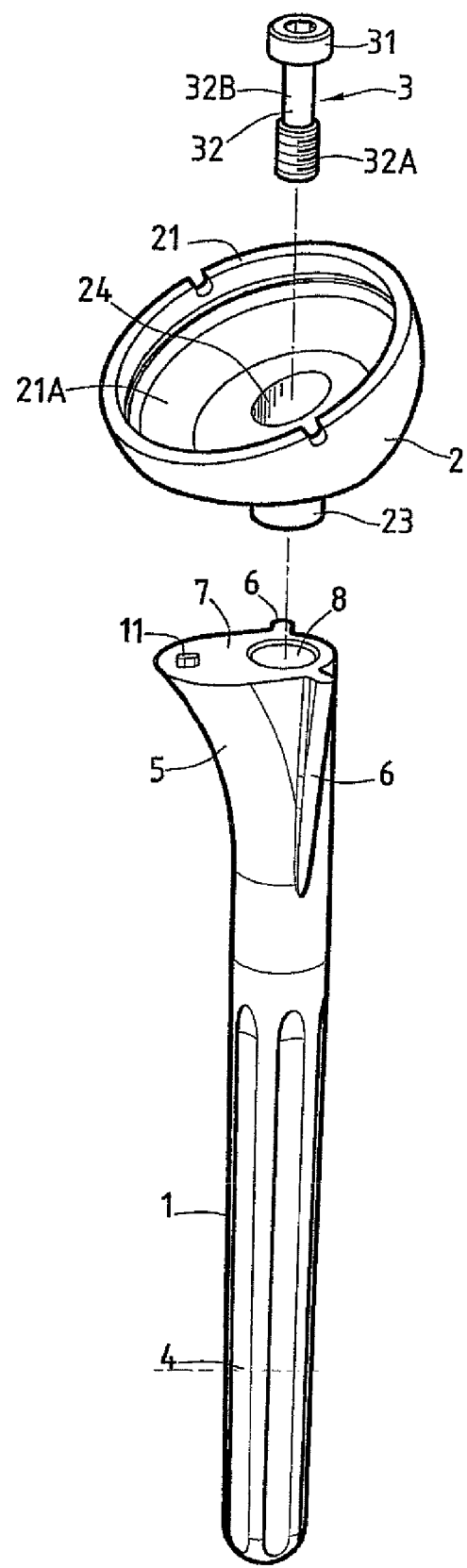

(52) U.S. Cl.
CPC ......... *A61F 2/40* (2013.01); *A61F 2002/3054* (2013.01); *A61F 2002/3071* (2013.01); *A61F 2002/30355* (2013.01); *A61F 2002/30428* (2013.01); *A61F 2002/30433* (2013.01); *A61F 2002/30604* (2013.01); *A61F 2002/30617* (2013.01); *A61F 2002/30774* (2013.01); *A61F 2002/30828* (2013.01); *A61F 2002/30879* (2013.01); *A61F 2002/4022* (2013.01); *A61F 2002/4051* (2013.01); *A61F 2002/4074* (2013.01); *A61F 2250/0089* (2013.01); *A61F 2250/0097* (2013.01)

(56) References Cited

U.S. PATENT DOCUMENTS

| | | | |
|---|---|---|---|
| 5,910,171 | A | 6/1999 | Kummer |
| 6,790,234 | B1 | 9/2004 | Frankle |
| 6,863,690 | B2 | 3/2005 | Ball |
| 7,169,184 | B2 | 1/2007 | Dalla Pria |
| 7,758,650 | B2 | 7/2010 | Dews |
| 9,622,869 | B2 * | 4/2017 | Nerot .................. A61F 2/4014 |
| 2001/0054624 | A1 | 12/2001 | Jourdin |
| 2004/0064187 | A1 | 4/2004 | Ball |
| 2004/0064190 | A1 | 4/2004 | Ball |
| 2004/0143335 | A1 | 7/2004 | Dews |
| 2004/0220673 | A1 | 11/2004 | Pria |
| 2004/0220674 | A1 | 11/2004 | Pria |
| 2011/0060417 | A1 | 3/2011 | Simmen |

FOREIGN PATENT DOCUMENTS

| | | | |
|---|---|---|---|
| EP | 0679375 | A1 | 11/1995 |
| EP | 0815810 | A1 | 1/1998 |
| EP | 1402854 | A2 | 3/2004 |
| EP | 1472999 | A1 | 11/2004 |
| FR | 2579454 | A1 | 10/1986 |
| FR | 2699400 | A1 | 6/1994 |
| FR | 2821545 | A1 | 9/2002 |
| WO | WO 1997025943 | A1 | 7/1997 |
| WO | WO 2003005933 | A2 | 1/2003 |
| WO | WO-03039411 | A1 * | 5/2003 ........... A61F 2/3601 |
| WO | WO 2006045949 | A2 | 5/2006 |

OTHER PUBLICATIONS

Translation of WO 03/039411A1 retrieved from espaceneton Jan. 12, 2019 (Year: 2019).*
Translation of FR2579454 retrieved from espacenet on Jun. 22, 2020 (Year: 2020).*
DUOCENTRIC®, Product Information Literature, Aston-Medical—Saint Etienne, France—to the best of our knowledge, 2007.

* cited by examiner

MODULAR HUMERAL PROSTHESIS FOR AN INVERTED SHOULDER PROSTHESIS

CROSS REFERENCE TO RELATED PCT APPLICATION

This application is a continuation of U.S. patent application Ser. No. 11/577,966, filed Oct. 25, 2005, now U.S. Pat. No. 9,622,869 which is a National Stage 35 U.S.C. 371 of International Patent Application PCT/FR2005/002663 filed Oct. 25, 2005, which claims priority to France Application No. 0411366, filed Oct. 25, 2004 (now abandoned) all of which are incorporated by reference in their entireties.

The present invention relates to a modular humeral prosthesis for an inverted shoulder prosthesis.

Shoulder prostheses consisting of a humeral prosthesis of which the epiphyseal portion cooperates with a mating deltoid component are known. In particular, anatomical shoulder prostheses in which the humeral prosthesis head is convex are known. These prostheses respect the orientation and the centre of rotation of actual joints. However, and in particular if the cap of the rotators is broken (partially or completely), prostheses of this type prevent elevation of the arm.

In order to re-establish the range of internal rotation of the arm (in particular elevation and abduction), the anatomical prosthesis is replaced by an inverted prosthesis in which the epiphyseal head of the humeral prosthesis is concave. An inverted prosthesis of this type displaces the centre of rotation of the shoulder and this increases the lever arm of the deltoid muscle and thus facilitates elevation of the arm. However, this displacement of the centre of rotation partially limits the internal and external rotations of the arm. In order to promote the internal rotation (which allows the patient to place his hand on his back), the epiphyseal head will be positioned with a retroversion of approximately 0° (frontal plane).

In addition to displacing the centre of rotation of the joint, the inverted shoulder prosthesis changes the angle of retroversion of the prosthesis relative to the shoulders. This modification to the shoulder retroversion angle varies from one patient to another. Therefore, when an inverted shoulder prosthesis is put into position, it has to be suitably orientated relative to the patient's individual anatomy. Similarly, it is desirable that the inverted prosthesis be put into position in such a way that the displacement of the centre of rotation of the shoulder does not cause an excessive distension of the deltoid muscle tendons.

In order to produce inverted shoulder prostheses, it has been proposed to use a single-piece humeral prosthesis of which the rod intended to cooperate with the humerus is generated by revolution and, in particular, is conical. A humeral prosthesis of this type has the advantage of being able to be orientated as desired relative to the humerus, but has the drawback of not being rotationally blocking with respect to the bone, with the result that the prosthesis is able to move and thus become dislodged over a period of time.

To overcome this drawback, it has been proposed to use a humeral prosthesis of which the rod has an anatomical shape, in other words a rod of which the cross-section cooperates with that of the metaphyseal portion of the medullary canal in a well-defined position. With an anatomical humeral rod of this type, however, it is necessary to be able to orientate the epiphyseal head of the prosthesis by rotation around the longitudinal axis of the rod. A modular humeral rod consisting of an anatomical rod and a separable epiphyseal head mounted on the anatomical rod by means of a ball joint, for example, has been proposed for this purpose (EP 1 402 805). This inverted shoulder prosthesis has the drawback of having an epiphyseal head which extends well above the epiphysis of the humerus (outside the humeral bone). This significantly increases the distance between the humerus and the glenoid cavity, over-tensing the deltoid muscle.

To avoid excessive extension of the deltoid muscle ligaments, the patent application US-2004/064187, in particular, has proposed a modular humeral rod for an inverted shoulder prosthesis comprising an anatomical rod on which is mounted a epiphyseal head designed to be integrated inside the epiphysis of the humerus and which can receive either a humeral head for an anatomical joint or a humeral head which mates with a concave joint for an inverted prosthesis. The epiphyseal head of this prosthesis can be orientated by rotation around the longitudinal axis of the humeral rod and can be locked in position relative to the humerus by means of vertical ribs provided in the epiphyseal head and which cooperate with the internal wall of the humeral canal. This prosthesis has the drawback of not having means for easy adjustment of the orientation of the epiphyseal head relative to the anatomical rod. One of the features of inverted shoulder prostheses equipped with an anatomical rod is that the orientation of the epiphyseal head relative to the anatomical rod has to be adapted to each patient. This orientation, which corresponds to the joint retroversion angle, can vary from 10° to 30°, depending on the patient and, in particular, on his age. It is therefore important to be able to adapt and control the orientation of the angle of the epiphyseal head relative to the anatomical rod in each individual case. In addition, when the prosthesis is in position, the angular adjustment of the epiphyseal head relative to the rod has to be locked to prevent it from becoming dislodged over a period of time.

The problem of locking the epiphyseal head in position relative to the rod could be solved by using single-piece anatomical humeral rods. However, the dimensions of the anatomical rod have to be adapted to the patient's size. In addition, the use of single-piece anatomical humeral rods would necessitate the provision of a very large number of rods each corresponding to a size and a retroversion angle. To reduce the number of prostheses required to be able to meet the requirements of all patients, therefore, it is desirable to have modular prostheses in which an epiphyseal head can be combined with an anatomical rod of adapted size, and the epiphyseal head can be orientated precisely relative to the anatomical rod when the prostheses is at rest and this orientation is secured.

In addition to this problem of reducing the number of parts required to meet all the requirements, it is desirable that the prosthesis can be removed in the event of an overhaul. Therefore, the humeral rod (adjusted angularly relative to the epiphysis) must never laterally exceed the epiphysis to allow extraction of the implant.

The object of the present invention is to overcome the drawbacks of known prostheses by proposing a modular humeral rod for an inverted shoulder prosthesis, which allows the epiphyseal head to be orientated precisely and securely relative to the metaphyseal portion of the anatomical rod (to optimize the internal rotation of the humerus), which may be extractable and which, when in position, is completely within the humerus to avoid over-tensing of the deltoid.

The invention accordingly relates to a modular humeral prosthesis for an inverted shoulder prosthesis comprising an anatomical rod which has an anatomical metaphyseal portion and a separable epiphyseal head which can be orientated angularly by rotation around the longitudinal axis of the anatomical rod, the anatomical rod and the epiphyseal head comprising mating means for angular indexing and for the mutual rotational blocking thereof.

The mating means for indexing and rotational blocking are, for example, on the one hand a plurality of notches provided in a contact surface of the epiphyseal head making contact with the numeral rod, disposed in a radial angular distribution around the longitudinal axis of the anatomical rod and, on the other hand, a lug carried by the other contact surface of the anatomical rod making contact with the epiphyseal head and capable of cooperating with said notches.

Preferably, the anatomical rod comprises at least one longitudinal rib for rotational blocking.

Preferably, the anatomical rod and the epiphyseal head comprise mating means for locating and guiding in rotation, and the epiphyseal head and the anatomical rod are joined together by a coaxial screw to the means of guidance in rotation.

Preferably, the joint between the anatomical rod and the epiphyseal head is intended to be located inside the humerus when the prosthesis is in position in order to respect the deltoid tension. It is therefore preferable that the contact surface of the epiphyseal head extends laterally beyond the anatomical rod.

Figure 2:
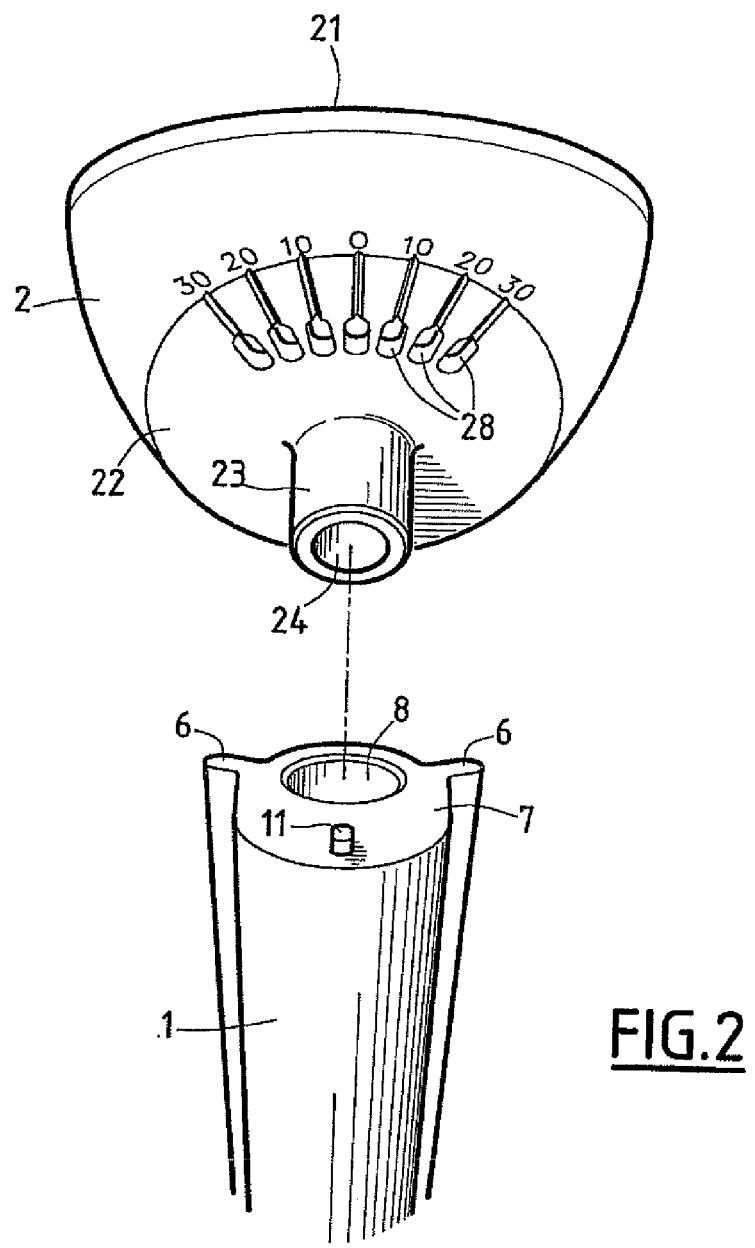
Figure 3:
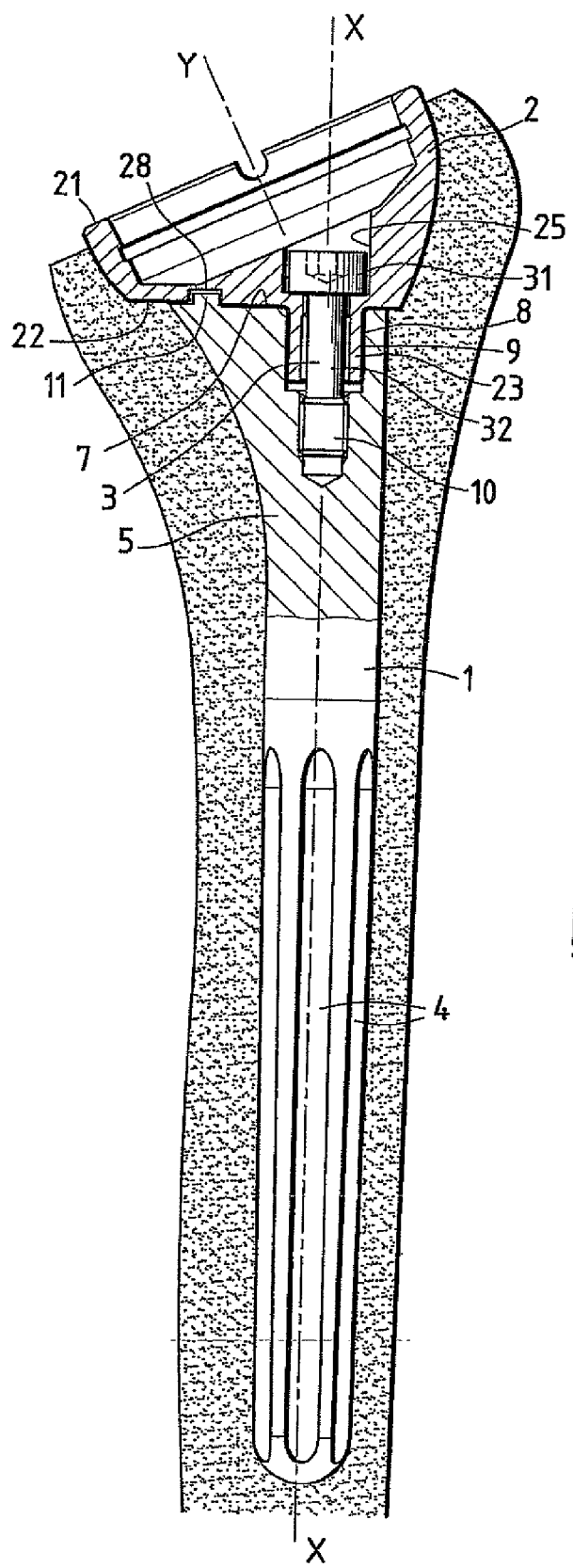

The invention will now be described in greater detail but in a non-limiting manner with reference to the accompanying figures, in which:

FIG. 1 is an exploded view of a modular humeral prosthesis for an inverted shoulder prosthesis, FIG. 2 is an enlarged view from below of the epiphyseal head and the upper portion of the anatomical rod of a modular humeral prosthesis for an inverted shoulder prosthesis, FIG. 3 is an exploded schematic section of a modular humeral prosthesis for an inverted shoulder prosthesis in position within a humerus.

Figure 4:
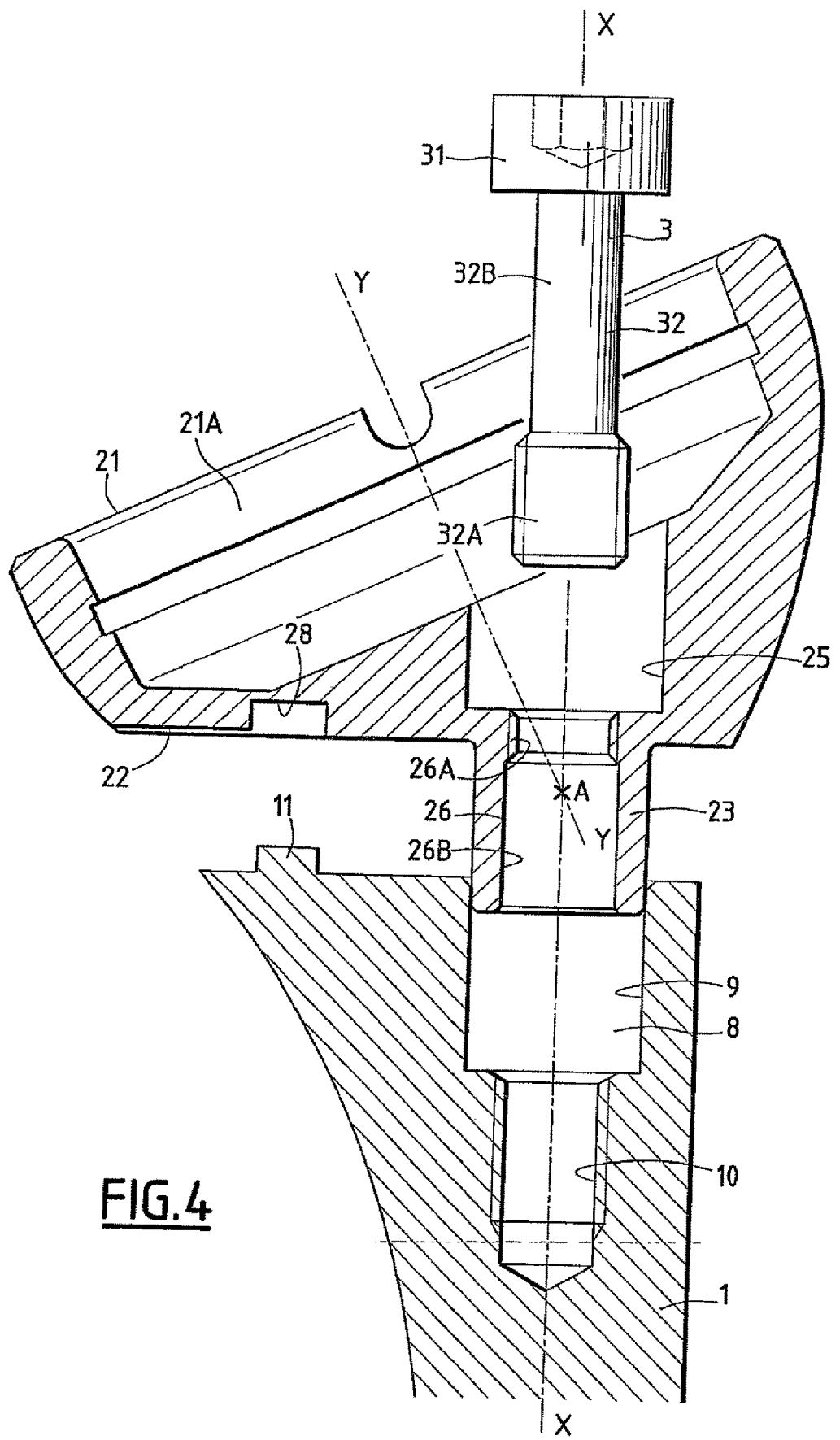

FIG. 4 is an enlarged longitudinal section of the upper portion of the modular humeral prosthesis in FIG. 3.

The modular humeral prosthesis for an inverted shoulder prosthesis shown in FIG. 1 comprises an anatomical rod 1, a separable epiphyseal head 2 which is positioned at the upper end (or proximal extremity) of the anatomical rod 1, and a screw 3 for connecting the epiphyseal head 2 to the rod 1.

The anatomical rod of which the shape is known per se comprises a generally cylindrical stem 4 which is extended in its upper portion by a metaphyseal portion 5 which flares upwardly so as to have a shape which is adapted to the form of the epiphyseal joint of a humerus with the metaphysis of this humerus. This head 5 constitutes the proximal extremity of the anatomical rod, the lateral wall of the head 5 of the anatomical rod comprises ribs 6 for blocking in position relative to a humerus in which the rod is implanted.

The proximal extremity of the anatomical rod 1 is limited by a planar surface 7 which corresponds to a section perpendicular to the longitudinal axis of the anatomical rod. A hole 8 extending within the anatomical rod and parallel to the axis of this rod is drilled perpendicularly to the surface 7 delimiting the proximal extremity. The hole 8 comprises a first bore 9 followed by a screw-threaded hole of smaller diameter 10. Preferably, the hole 8 and the stem 4 of the anatomical rod are coaxial. The surface 7 further comprises a lug 11 which projects longitudinally relative to the metaphyseal rod.

The epiphyseal head 2 is a portion of a sphere delimited by an equatorial plane 21 and a plane forming an acute angle with an equatorial plane. Below the equatorial plane 21, the epiphyseal head 2 comprises a bowl 21A intended to receive a polyethylene or ceramic cup. This cup is the part which is intended to cooperate with the mating portion of the prosthesis which will be fixed to the scapula. The plane forming an acute angle with the equatorial plane defines a polar surface 22 intended to come into contact with the end surface 7 of the anatomical metaphyseal rod 1.

The polar surface 22 comprises a cylindrical lug 23 which projects from the polar surface 22 and is perpendicular thereto. The size of this cylindrical lug 23 is adapted so that it can cooperate with the greater diameter bore 9 of the axial hole 8 in the anatomical rod and thus locate the epiphyseal head relative to the anatomical rod. An axial hole 24 for receiving a screw 3 extends through the cylindrical lug 23, the screw 3 extending both in the hole 24 in the epiphyseal head and in the hole 8 in the anatomical rod so that it will be screwed into the screw-threaded portion 10 of the hole 8. The hole 24 comprises a first portion 25 of greater diameter intended to receive the head 31 of the screw and a portion of smaller diameter 26 intended to receive the body 32 of the screw 3. The cylindrical lug 23 and the hole 8 constitute means for locating and guiding in rotation the epiphyseal head relative to the anatomical rod.

The portion of smaller diameter 26 comprises a first portion 26A of short length having a diameter and a screw thread identical to the diameter and screw thread of the screw-threaded portion 10 of the axial hole 8, the metaphyseal rod and a second portion 26B of greater length extending to the point where the hole emerges at the end of the cylindrical lug 23 and of which the diameter is greater than or equal to the external diameter of the screw-threaded portion of the screw 3. The body 32 of the screw 3 comprises, at its extremity, a screw-threaded end 32A which is capable of cooperating with the screw thread of the screw-threaded portion 10 of the axial hole 8 in the metaphyseal rod, and a stem 32B connecting the head 31 of the screw 3 to the screw-threaded end, and having a diameter smaller than the internal diameter of the first screw-threaded portion 26A of the portion of smaller diameter 26 of the hole 24 in the epiphyseal head.

With this arrangement, the epiphyseal head is completely separated from the anatomical rod by unscrewing the screw. In order to put the screw in position, it first has to be screwed into the screw-threaded portion 26A of the hole in the epiphyseal head. This has the advantage of making the screw integral with this epiphyseal head while leaving it free in rotation and in translation over a specific length and thus facilitates manipulation by the surgeon who is putting the prosthesis in position.

The polar surface 22 comprises a plurality of notches 28 disposed radially relative to the axis of the cylindrical lug 23 and at a distance from this lug such that, when the cylindrical lug 23 is disposed inside the hole 8 of the anatomical rod 1, the lug 11 situated on the surface 7 of the proximal extremity of the anatomical rod 1 can cooperate with a notch 28. These notches are arranged at 10° from one another in a fan and are complemented by markings which allow the position of the epiphyseal head 2 relative to the anatomical rod 1 to be determined when the epiphyseal head is disposed on the anatomical rod and the lug 11 is within a notch 28.

In addition, the plane defining the polar surface 22 is selected so that the diameter of this polar surface is sufficient for the polar surface 22 to extend laterally beyond the surface 7 of the proximal extremity of the anatomical rod, whatever the orientation of the epiphyseal head relative to the anatomical rod. As a result, when the prosthesis is in position in a humerus, the re-growing bone does not form bands which extend beyond the proximal extremity of the anatomical rod and therefore does not prevent extraction of the prosthesis.

Referring to FIG. 4, the epiphyseal head 2 is able to rotate about the longitudinal axis XX of the anatomical rod. The axis YY of the epiphyseal head perpendicular to the equatorial plane 21 intersects the longitudinal axis XX of the anatomical rod 1 at a point A preferably located on a surface defined by the contact between the proximal face 7 of the anatomical rod 1 and the polar face 22 of the epiphyseal head 2.

Finally, FIG. 3 shows that the length of the anatomical rod and the dimensions of the epiphyseal head are selected so that, when the prosthesis is in position, the epiphyseal head is completely included in the epiphysis of the humerus.

In order to put a prosthesis of this type in position, the surgeon begins by preparing the humerus by producing, in a known manner, an axial hole adapted to receive an anatomical humeral rod and an epiphyseal head. Then, using an appropriate gauge, he determines the retroversion which the epiphyseal head will have to perform relative to the anatomical humeral rod.

The surgeon then puts in position the anatomical rod then the epiphyseal head while orientating it at a predetermined angle and immobilises it in rotation by causing the lug 11 of the proximal extremity of the anatomical rod to cooperate with the appropriate groove 28 in the polar surface 22 of the epiphyseal head. He finally tightens the screw 3 to lock the assembly.

The invention claimed is:

1. A modular humeral prosthesis comprising:
    an anatomical stem having a longitudinal axis and including a hole;
    a separable epiphyseal head which may be oriented angularly by rotation about the longitudinal axis of the anatomical stem and includes an axial hole;
    a first contact surface on the epiphyseal head and a second contact surface on the anatomical stem, the first and second contact surfaces being in contact with each other;
    the second contact surface being planar, perpendicular to the longitudinal axis and constituting a proximal extremity of the anatomical stem;
    a screw which may pass through the axial hole provided in the epiphyseal head and into the hole in the anatomical stem to connect the epiphyseal head to the anatomical stem;
    indicia of rotation between the epiphyseal head and the anatomical stem;
    wherein the first contact surface extends laterally beyond the second contact surface of the anatomical stem whatever the angular orientation of the epiphyseal head with respect to the anatomical stem; and
    wherein the epiphyseal head comprises a socket for receiving a cup of a reverse shoulder prosthesis cooperating with a scapular prosthesis.

2. The modular humeral prosthesis according to claim 1 and further comprising a plurality of notches provided on the first contact surface disposed according to a radial angular distribution about the longitudinal axis of the anatomical stem, and the anatomical stem includes a peg borne by the second contact surface and capable of cooperating with the notches.

3. The modular humeral prosthesis according to claim 1, wherein the anatomical stem comprises at least one longitudinal rib for rotational locking.

4. The modular humeral prosthesis according to claim 1, wherein a junction between the anatomical stem and the epiphyseal head is intended to be located inside a humerus when the prosthesis is in place, in order to take account of deltoid tension.

5. The modular humeral prosthesis according to claim 1, wherein the indicia of rotation are provided in degrees of rotation.

* * * * *